United States Patent
Lindegren

(10) Patent No.: US 6,188,932 B1
(45) Date of Patent: Feb. 13, 2001

(54) IMPLANTABLE ELECTRODE LEAD

(75) Inventor: Ulf Lindegren, Enskede (SE)

(73) Assignee: Pacesetter AB, Järfälla (SE)

(*) Notice: Under 35 U.S.C. 154(b), the term of this patent shall be extended for 0 days.

(21) Appl. No.: 09/308,201

(22) PCT Filed: Nov. 6, 1997

(86) PCT No.: PCT/SE97/01862
§ 371 Date: Jul. 6, 1999
§ 102(e) Date: Jul. 6, 1999

(87) PCT Pub. No.: WO98/20933
PCT Pub. Date: May 22, 1998

(30) Foreign Application Priority Data

Nov. 13, 1996 (SE) .................................................. 9604143

(51) Int. Cl.[7] .................................................. A61N 1/05
(52) U.S. Cl. .................................................. 607/126
(58) Field of Search .................................. 607/126, 128, 607/122

(56) References Cited

U.S. PATENT DOCUMENTS 4,796,643  1/1989  Nakazawa et al. .
4,883,070  11/1989  Hanson .
5,179,962  1/1993  Dutcher et al. .

FOREIGN PATENT DOCUMENTS 0 041 254  12/1981  (EP) .
0 408 358  1/1991  (EP) .
0 573 334  12/1993  (EP) .

*Primary Examiner*—Scott M. Getzow
(74) *Attorney, Agent, or Firm*—Schiff Hardin & Waite

(57) ABSTRACT

An implantable electrode lead has a proximal end intended for connection to, e.g., a pacemaker and has a distal end with an electrode head equipped with an external, tine-type anchoring unit. The anchoring unit has a number of projections which are integrally formed as a one-piece unit together with a ring-shaped carrier. The carrier is made of an elastic material, and is disposed under elastic tension in an annular groove in the exterior of the electrode head, which fixes the position of the anchoring unit relative to the electrode head. The anchoring unit detaches from the electrode head, by the carrier being pulled out of the groove, when a predetermined, minimum pulling force is exerted on the electrode head from the proximal end of the lead.

9 Claims, 1 Drawing Sheet

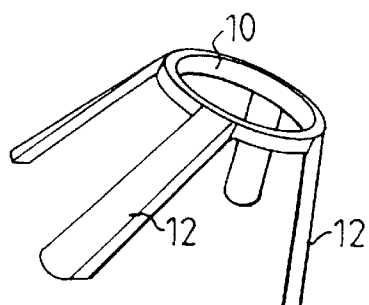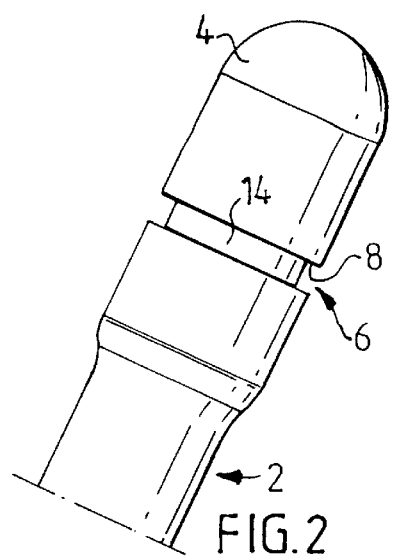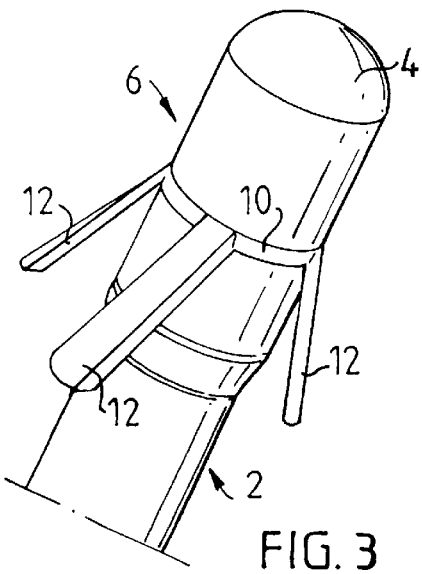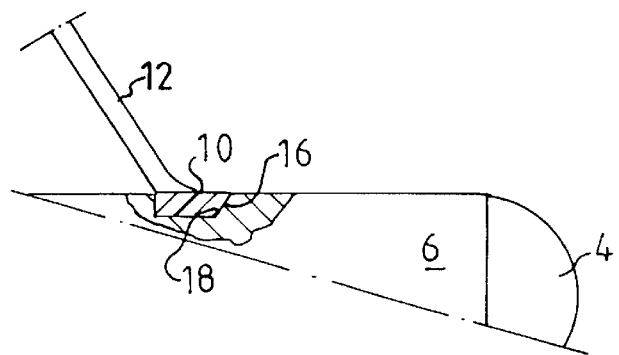

IMPLANTABLE ELECTRODE LEAD

BACKGROUND OF THE INVENTION

1. Field of the Invention

The present invention relates to an implantable electrode lead with a proximal end intended for connection to e.g. a heart stimulator or some other device for electrical stimulation or sensing, primarily in the human body, and a distal end with an electrode head equipped with external anchoring elements, such as tine-like position-fixation elements,

2. Description of the Prior Art

An electrode lead of of the above type can either serve as an implant or be removed from the body after treatment is concluded.

To prevent a recently implanted endocardiac electrode from being dislocated, i.e. from being displaced from its intended position in the heart, it is important for the electrode to be anchored to heart muscle in some suitable fashion. This is especially important the first few days after the implantation, when heart tissue (fibrin) will not have had time to cover or grow around the electrode, thereby achieving natural anchoring of the head.

The endocardiac electrode, arranged on the distal end of its associated electrode lead, is therefore usually equipped with some kind of anchoring means. Conical collars, tines and fins located immediately behind the contact electrode, which is usually a point electrode on the distal end of the electrode lead, are examples of such anchoring means for position-fixation. The purpose of such anchoring means is to cause entanglement or wedging of the endocardiac electrode in the trabeculae in the interior of the heart. Electrodes equipped with tines have proved to be highly effective in achieving reliable anchoring at the desired position in the heart.

When a previously implanted electrode lead has to be removed from the heart for some reason or if its endocardiac electrode requires repositioning in the heart, detaching the electrode from the trabeculae may prove difficult because the electrode's anchoring means have become entangled in the trabeculae or anchored in place by the growth of fibrin onto or around the anchoring means.

Removing the entire electrode lead from the heart or retracting the lead and its contact electrode head a short distance can therefore be much more difficult because of problems in detaching the fixation means from the heart tissue in which they have become entangled or stuck.

In practice, it is often, but not always, possible to detach the end of the electrode lead with the anchoring means from its anchored position in the heart by the application of adequate tractive force.

However, detachment this way can damage the heart tissue, in which the anchoring means are embedded or stuck, to varying degrees.

One electrode lead, known from U.S. Pat. No. 5,179,962, has a distal end section consisting of an electrode head with pin-like fixation means. These fixation means can be switched to/from a retracted, inactive position in which they are completed withdrawn inside the electrode head, or an active position in which they, like times, project at an angle to the rear from the exterior of the electrode head in an area thereof located a short distance from the electrode head's electrode contact surface on the free outer end of the electrode head.

The pin-like position-fixation means are switched between the active and inactive positions with the aid of a stylet, which can move axially inside the electrode lead and electrode head, whose anterior end is attached to a piston-like, sliding holder, inside the electrode head, to which the inner, anterior ends of the anchoring means are attached. The free, posterior parts of the fixation means project to the rear from the holder and then at an angle up through guide holes in a sleeve, made of an electrically insulating material, which encloses the electrode head.

However, this known electrode lead with a retractable, deployable position-fixation means in the electrode head is a constructively complex design, especially as regards the electrode head. A constructively complex electrode lead and electrode head make the design unavoidably expensive.

European Application 0 041 254 discloses an electrode lead which at its distal end contains a harpoon-like component. The harpoon-like element is normally located and held in a longitudinal cavity in the distal end of the electrode lead. The harpoon-like element can be extended from the end of the lead, for instance by means of an internal stylet in the lead, and anchored to the endocavitary wall. Should it be necessary to remove the electrode lead, the harpoon-like element can be pushed entirely out from and released from the electrode lead. The lead then can be removed, the harpoon-like element remaining in the endocavitary wall.

European Application 0 041 254 discloses an electrode lead, which at its distal end is provided with a detachable sleeve. The sleeve is provided with anchoring means in the form of tines. The sleeve is held releasably on the exterior of the distal end, for instance by means of a press fit. In this way the lead can be removed from the heart., leaving the sleeve in the heart.

SUMMARY OF INVENTION

An object of the present invention is to provide an implantable electrode lead whose electrode head, equipped with external anchoring elements, can be easily detached from the anchoring elements when the elements are stuck in the interior of the heart and there is a concomitant need to remove the electrode lead from the heart, e.g. to replace the lead with a new electrode lead.

The above object is achieved in accordance with the principles of the present invention in an implantable electrode lead having an anchoring unit formed by two or more thin-like or time-like projections and a ring-shaped carrier for the projections, the carrier surrounding the electrode head and having a radially inward portion which is received in a circular channel in the electrode head, the anchoring unit being detachable from said electrode head, by being pulled out of said channel, when acted upon by a predetermined minimum extraction force exerted at a proximal end of the electrode head. The proximal end of the electrode head, as used herein, means the end of the electrode head opposite the electrode tip.

The number of anchoring elements or projections is not decisively important to the present invention but is selected with a view to the anchoring capability desired for the electrode head with the selected embodiment of the respective anchoring means. In practice, four anchoring elements or projections, evenly distributed around the circumference of the electrode head, have been found to produce very good results. However, a larger number of anchoring elements can also be expected to display good anchoring characteristics.

As noted above, the position-fixation structure which holds the anchoring unit on the electrode head is a groove encircling the exterior of the electrode head. This groove is then appropriately dimensioned to admit at least the radial inner parts of the ring-shaped tine-bearing a carrier.

From the manufacturing point of view, having the projections devised as an integral part of a one-piece ring-shaped carrier and evenly distributed around the circumference of the ring-shaped carrier, should be preferable. The projections and their associated ring-shaped carrier are preferably made of an elastic material such as silicone rubber.

In its unmounted state, the ring-shaped carrier preferably has an inner diameter which is at least slightly smaller than the diameter of the axial part of the electrode head onto which the ring-shaped means is to be mounted. An appropriate retention force (clamping force) can be achieved for the ring-shaped carrier in question by the choice of an appropriate diameter for the hole in the ring-shaped carrier and the diameter of the axial section onto which the ring-shaped carrier is to be mounted and by the choice of an appropriate elastic material of which the ring-shaped carrier and projections are made.

If the axial section onto which the ring-shaped carrier is to be mounted consists of the part of the electrode head which is encircled by a position-fixation groove in same, a ring-shaped carrier made of e.g. silicone rubber would function about like a stretched "rubber band" arranged in the position-fixation groove.

It may be appropriate in some instances, particularly if the attachment units (ring-shaped carrier) is made of a less elastic material than e.g. silicone rubber, to devise the position- fixation groove and the ring-shaped carrier in a way facilitating detachment of the ring-shaped carrier from the fixation groove and, accordingly, detachment from the electrode head when a detachment force is exerted.

DESCRIPTION OF THE DRAWINGS

FIG. 1 is a perspective view of ring-shaped carrier, equipped with projections to form an anchoring unit, according to the invention.

FIG. 2 is a side view showing the distal end section of an electrode lead with a position-fixation groove in the electrode head.

FIG. 3 is a perspective view of the distal end section of the electrode lead with a ring-shaped carrier mounted in the position-fixation groove according to FIG. 1.

FIG. 4 shows, on a larger scale and in partial longitudinal section, a somewhat different embodiment of the ring-shaped carrier and position-fixation groove for an electrode lead according to the invention.

DESCRIPTION OF THE PREFERRED EMBODIMENTS

The invention relates to an implantable electrode lead 2 (see FIGS. 2 and 3) used for carrying electrical impulses between a heart stimulator (not shown), on the one hand, and a contact electrode 4 in contact with the interior of the heart, on the other hand. In the conventional manner, the electrode lead 2 is equipped with a connector pin at its proximal end (not shown), and the contact electrode 4 is located on the end of an electrode head 6 arranged on the distal end of the electrode lead 2, as shown in FIGS. 2 and 3. The connector pin on the proximal end of the electrode lead is for electrical connection of the electrode lead to a heart stimulator. The exterior of the electrode head 6 is provided with position-fixation structure in the form of an encircling position-fixation groove 8 designed to admit a ring-shaped carrier 10, encircling the electrode head 6, equipped with four projections 12, extending at an angle outward and to the rear, whose task is to anchor the electrode head 6 in the interior of heart muscle in order to insure reliable contact between the tip electrode 4 and heart muscle. In this instance the projections 12 consist of tine-like position-fixation elements.

The groove 8 is sized to admit at least most of the ring-shaped carrier 10 with the projections 12. The projections 12, which are devised as integral part of the one-piece ring-shaped carrier 10, are evenly distributed around the circumference of the ring-shaped carrier 10. In its unmounted state shown in FIG. 1, the ring-shaped carrier 10 has an inner diameter which is smaller than the diameter of the part 14 of the electrode 6 in which the position-fixation groove 8 is arranged. The anchoring unit, consisting of the ring-shaped carrier 10 and the projections 12, is made of silicone rubber or some other biocompatible material with about the same elasticity as silicone rubber. Since the ring-shaped carrier 10 is an elastic ring whose inner diameter is smaller than the axial section 14 of the electrode head 6, the anchoring unit 10, 12 can be forced onto the electrode head from the head's free, proximal end and installed elastically pre-tensioned in the position-fixation groove 8, thereby resulting in the configuration shown in FIG. 3.

If, for some reason, the implanted electrode lead 2 needs to be removed from the heart by the application of a tractive force on the proximal end (not shown) of the electrode lead 2, extraction may be made more difficult or even impossible because the projections 12 are too firmly anchored in the trabeculae in the interior of the heart. Since projections 12 according to the invention are now detachably mounted on the exterior of the electrode head, being only elastically retained on the electrode head by the ring-shaped carrier 10 arranged like a "rubber band" in the position-fixation groove 8, the electrode head 6 can still be detached from the anchoring unit 10, 12, embedded in the heart, because the unit detaches from the groove 8 when a specific tractive force is applied to the electrode lead 2. In other words, the electrode head 6 and the anchoring unit 10, 12 embedded in the heart separate when a pre-defined minimum extraction force acts on the projections 12 towards the free end of the electrode head 6 equipped with the tip electrode 4.

To facilitate detachment of the ring-shaped carrier 10 from the fixation groove 8, thereby facilitating detachment of the anchoring unit 10, 12 from the electrode head when the electrode lead 2 is retracted, the mounting of the ring-shaped carrier 10 in the groove 8 can have a somewhat different design than the one shown in FIGS. 1–3. This embodiment version is shown in FIG. 4.

In this instance, the ring-shaped carrier 10 has a beveled, forward-outward anterior lateral edge area 18 which presses against a lateral edge area, with a corresponding forward-outward bevel, forming the anterior, lateral end of the grooves. Application of the pre-defined minimum extraction force to the anchoring unit 10, 12 facilitates separation of the anchoring unit and electrode head 6 because the lateral edge area 16 of the ring-shaped carrier 10 can slide more easily out of the groove 8 as a result of the anterior, lateral beveled edge area 18 of the groove 8.

The width of the groove 8 preferably should be between 1 to 2:5 times the depth of the groove 8.

It should be noted that the resilience of the tines in some circumstances will make it possible to disengage the anchoring unit before the above-mentioned predefined minimum extraction force has been attained, since the tines may deflect to a sufficient extent to allow the tines to disengage from for instance the trabeculae.

Although modifications and changes may be suggested by those skilled in the art, it is the invention of the inventor of embody within the patent warranted hereon all changes and modifications as reasonably and properly come within the scope of his contribution to the art

What is claimed is:

1. An electrode head for an implantable medical electrode lead, comprising:

an electrode head body terminating at a tip end and having an end opposite said tip end adapted for connection to an electrical conductor;

an anchoring unit having a ring-shaped carrier and a plurality of anchoring elements projecting radially outwardly from said carrier, said carrier having a radially inner portion; and said electrode head body having an annular groove proceeding around said electrode head body and disposed between said tip end and said end opposite said tip end, at least said radially inner portion of said carrier being received in said groove and being releasably held therein so as to be detached from said electrode head body when said electrode head body is acted on by a predetermined pulling force exerted on said end of said electrode head body opposite said tip end.

2. An electrode head as claimed in claim 1 wherein said annular groove has a lateral edge at a side of said groove closest to said tip end said lateral edge having a radially outwardly proceeding bevel, and said carrier having a lateral edge with a bellow complementary to said bevel of said lateral edge of said groove, for facilitating detachment of said carrier from said groove when said predetermined pulling force is exerted.

3. An electrode head as claimed in claim 1 wherein said ring-shaped carrier and said plurality of anchoring elements comprise a unitary, one-piece anchoring unit, and wherein said projections are disposed at uniform spacings around a circumference of said carrier.

4. An electrode head as claimed in claim 1 wherein said carrier, prior to being disposed in said groove, has an inner diameter which is slightly smaller than a diameter of said electrode head body.

5. An electrode head as claimed in claim 1 wherein said projections and said carrier are composed of an elastic material.

6. An electrode head as claimed in claim 5 wherein said elastic material is silicone rubber.

7. An electrode head as claimed in claim 1 wherein said groove has a width and a depth with said width being between 1 and 2.5 times said depth.

8. An electrode head as claimed in claim 1 wherein said projections respectively comprise tines.

9. An electrode head as claimed in claim 1 wherein said projections respectively comprise fins.

* * * * *